(12) United States Patent
Bae et al.

(10) Patent No.: US 7,163,919 B2
(45) Date of Patent: Jan. 16, 2007

(54) ANTICANCER COMPOSITION

(76) Inventors: Seog-Nyeon Bae, 3-1406 Garak Daerim Apt., Bangi-dong, Songpa-gu, Seoul, Republic of Korea (KR) 138-0950; Lae-Ok Park, 12-30 Bangbaebon-dong, Seocho-gu, Seoul, Republic of Korea (KR) 137-814

( * ) Notice: Subject to any disclaimer, the term of this patent is extended or adjusted under 35 U.S.C. 154(b) by 0 days.

(21) Appl. No.: 10/508,268

(22) PCT Filed: Mar. 17, 2003

(86) PCT No.: PCT/KR03/00514

§ 371 (c)(1),
(2), (4) Date: May 24, 2005

(87) PCT Pub. No.: WO03/077899

PCT Pub. Date: Sep. 25, 2003

(65) Prior Publication Data

US 2005/0255173 A1    Nov. 17, 2005

(30) Foreign Application Priority Data

Mar. 16, 2002 (KR) ............... 10-2002-0014342
Oct. 31, 2002 (KR) ............... 10-2002-0067291

(51) Int. Cl.
*A61K 38/38* (2006.01)
*C07K 14/76* (2006.01)

(52) U.S. Cl. ........................ 514/12; 530/362

(58) Field of Classification Search ............... None
See application file for complete search history.

(56) References Cited

U.S. PATENT DOCUMENTS 4,191,749 A * 3/1980 Bryant ............ 424/561

6,133,317 A   10/2000 Hart ............ 514/574

FOREIGN PATENT DOCUMENTS

WO         01/85178 A1 * 11/2001
WO         WO 01/85178   11/2001

OTHER PUBLICATIONS

Kavanagh et al., Prostate, 1994, 24(3): 139-142.*
Sorensen et al., Molecular Human Reproduction, 1999, 5(4): 331-337.*
Therien et al., Biology of Reproduction, 1999, 61: 590-598.*
Jain et al., Barriers to Drug Delivery in Solid Tumors, Scientific American, Jul. 1994, pp. 58-65.*
Amano et al., "Fluorescence Spectra From Human Semen And Their Relationship With Sperm Parameters," Archives of Andrology 36:9-15 (1996).*
Costello et al., "The Intermediary Metabolism of the Prostate: A Key to Understanding the Pathogenesis and☐☐Progression of Prostate Malignancy," Oncology 2000; 59:269-282☐☐.*

* cited by examiner

*Primary Examiner*—Robert A. Wax
(74) *Attorney, Agent, or Firm*—Sheridan Ross P.C.

(57) ABSTRACT

The present invention relates to an anticancer composition comprising a therapeutically effective amount of one or more active components selected from the group consisting of citric acid; citric acid and zinc; citric acid and albumin; and citric acid, zinc and albumin, and a pharmaceutically acceptable carrier. The anticancer composition of the present invention has strong anticancer activity, and in addition does not have harmful side effects.

2 Claims, 13 Drawing Sheets

Marker Control  2   4   6   12   24   48   72   96 hrs
Time after treatment with the anticancer composition 3   6   12   24hrs
Time after treatment with
the anticancer composition Control　30min　1hrs　3hrs　6hrs　9hrs　12hrs Time after treatment with the anticancer composition Control | Treatment with the anticancer composition

ANTICANCER COMPOSITION

This application is a 371 of PCT/KR03/00514, filed Mar. 17, 2003.

TECHNICAL FIELD

The present invention relates to an anticancer composition, more particularly, to an anticancer composition comprising a therapeutically effective amount of one or more active components selected from the group consisting of citric acid; citric acid and zinc; citric acid and albumin; and citric acid, zinc and albumin, and a pharmaceutically acceptable carrier.

PRIOR ART

With the development of chemotherapy, survival and recovery rates of cancer patients have improved. However, anticancer agents are problematic in terms of being highly toxic and thus severely damaging normal cells. To overcome such a side effect of anticancer agents, many recent studies have focused on developing alternative anticancer substances capable of specifically suppressing proliferation of tumor cells, leading to finding many candidates having anticancer activity. Such anticancer compounds are disclosed in International Pat. Publication Nos. WO 96/40142, WO 97/40142, WO 97/13771 and WO 95/23141. However, the newly discovered anticancer compounds, which specifically suppress proliferation of tumor cells, are chemically synthesized and thus have a potential to induce severe side effects in the body.

Such a disadvantage of the conventional anticancer agents drove many researchers to develop anticancer agents having mild side effects as well as excellent anticancer activity, and some of them have attempted to find natural substances having anticancer activity. In this regard, the present inventors were interested in the fact that natural human seminal fluid had anticancer effect versus epithelial ovarian cancer.

Epithelial ovarian cancer is the most common type of ovarian cancer, and a major cause of death by malignancy in gynecological oncology. The high mortality of patients with epithelial ovarian cancer is due to insidious development of epithelial ovarian cancer, causing most patients to recognize significant symptoms at a considerably advanced stage (Ozols, R. F. Semin. Oncol., 1995, Vol. 22, p 61.). Despite removal of tumor by surgical operation or positive chemotherapy, only 20–30% of patients with epithelial ovarian cancer survive owing to rapid emergence of drug resistance.

Until now, risk factors and causes of epithelial ovarian cancer are still not well known. However, a large number of studies suggest that there is a relationship between frequency of ovulation and development of epithelial ovarian cancer, and such a relationship is demonstrated by the fact that incidence of epithelial ovarian cancer is increased for young and old women (early menarche and late menopause), for non married women, and for nulliparous women (Franceshi et al. Int. J. Cancer, 1991, Vol. 49, p 57; Taylor et al. Cancer, 1959, Vol. 12, p 1207; Fraumeni et al. J. Natl. Cancer Inst., 1969, Vol. 42, p 455; Weiss et al. J. Natl. Cancer Inst., 1977, Vol. 58, p 913; Nergri et al. Int. J. Cancer, 1991, Vol. 49, p 50; Stanford, J. L. Contraception 43, 1991, p 543; and Franceshi et al. Int. J. Cancer, 1991, Vol. 49, p 61.). On the other hand, oral contraceptives are generally known to have protective effect versus development of epithelial ovarian cancer.

According to a popular theory, epithelial ovarian cancer occurs by repeated division and repair of the ovarian surface epithelium during ovulation (Fathalla, M. F. Lancet., 1971, Vol. 2, p 163.). During recovery of the epithelial surface, transformed epithelial cells are spontaneously mutated, tumor-suppressor genes are inactivated, and oncogenes are easily activated by carcinogens.

On the other hand, the human seminal fluid has been reported to have the following physiological functions and anticancer effects. The seminal plasma repairs immunological damage to sperm caused by cytotoxic lymphocytes after sexual intercourse (Stities et al. Nature, 1975, Vol. 253, p 727; James et al. Immunol., 1985, Vol. 6, p 61.), and the human seminal fluid inhibits development of humoral immunity and in vivo growth of tumor (Anderson et al. Immunol., 1985, Vol. 128, p 535; and Michaelis et al. Anticancer Drugs, 2000, Vol. 11, p 369.). Also, the human seminal fluid influences production of matrix metalloproteinase (MMP)-2 and MMP-9 mRNA in cervical epithelial carcinoma cells, and thus is believed to affect progression of cervical cancer upon sexual activity (Jeremias et al. Am. J. Obstet. Gynecol., 1999, Vol. 181, p 591.). According to a recent report, bovine seminal ribonuclease (BS-RNase) induces apoptosis in human lymphocytes and human tumor cells in time and dose-dependent manners. BS-RNase exerts selective cytotoxicity to neuroblastoma (NB) cells resistant to chemotherapeutic drugs (Cinatl et al. Anticancer Res., 2000, Vol. 20, p 853; Cinatl et al. Int. J. Oncol., 1999, Vol 15, p 1001.).

In addition, Gjorgov performed ecological research on anticancer effects of seminal fluid by comparing various cases, in which relations between reduced exposure to the human seminal fluid and incidence of breast cancer were investigated. In this research, when comparing incidence risk of breast cancer in women using barrier contraceptives (condom) to that in women using non-barrier contraceptives (contraceptive drugs, intra uterine device (IUD), rhythm control, or tubal ligation), women using barrier contraceptives (condom) were found to have 5.2-fold higher incidence of breast cancer (Gjorgov et al. Folia Med., 1998, Vol. 40, p 17.).

Major components of the seminal fluid having anticancer activity as described above include albumin, lactoferrin, transferrin, immunoglobulins, acid phosphatase, L-carnitine, L-arginine, L-histidine, citric acid, fructose, magnesium, zinc, prostaglandin, and glycerophosphocholine.

DISCLOSURE OF THE INVENTION

Based on the fact that reduced exposure to the human seminal fluid during the period of ovulation is an etiological risk factor in epithelial ovarian cancer progression, the present inventors concluded that the human seminal fluid is able to effectively remove malignant transformed epithelial cells.

Therefore, the present invention provides anticancer compositions, as follows.

In an aspect, the present invention provides an anticancer composition comprising a therapeutically effective amount of citric acid and a pharmaceutically acceptable carrier.

In another aspect, the present invention provides an anticancer composition comprising therapeutically effective amounts of citric acid and zinc, and a pharmaceutically acceptable carrier.

In a further aspect, the present invention provides an anticancer composition comprising therapeutically effective amounts of citric acid and albumin, and a pharmaceutically acceptable carrier.

In a still further aspect, the present invention provides an anticancer composition comprising therapeutically effective amounts of citric acid, zinc and albumin, and a pharmaceutically acceptable carrier.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
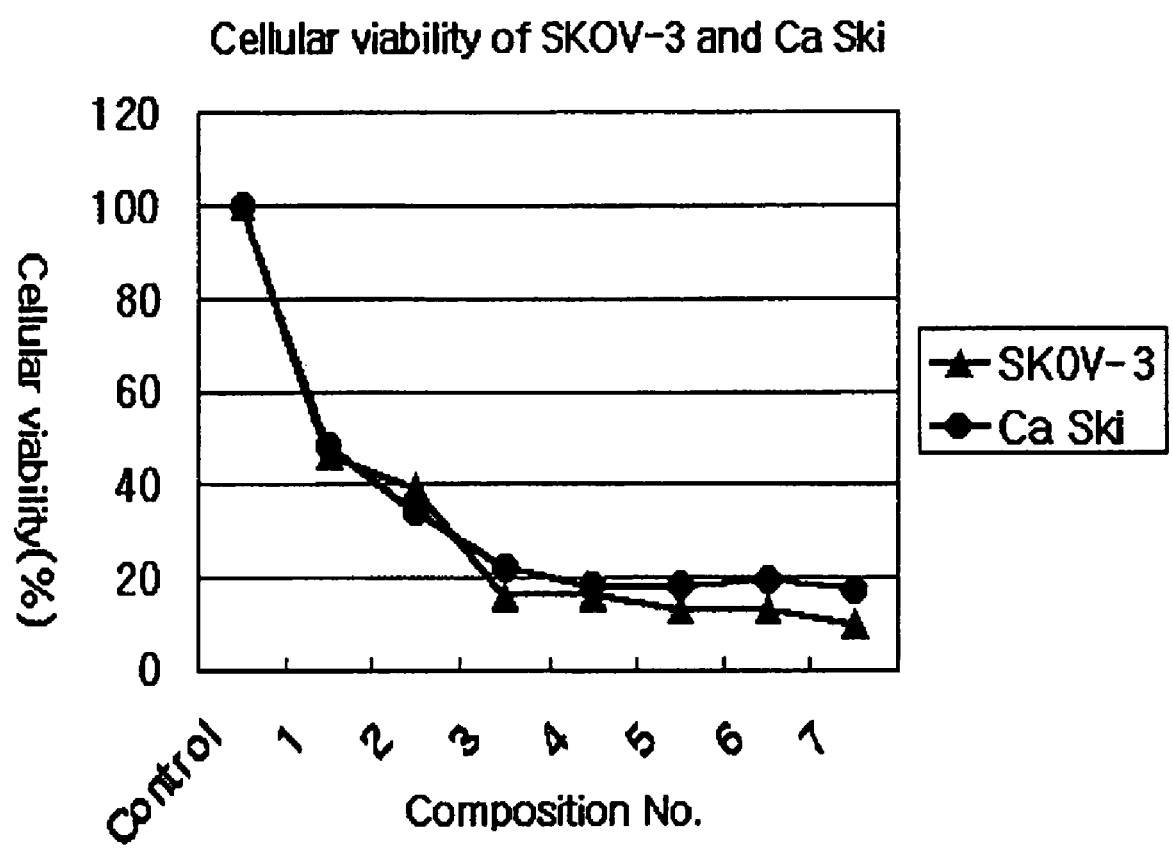
FIG. 1 is a graph showing effects of an anticancer composition comprising citric acid as an active component according to the present invention on viability of the human ovarian adenocarcinoma cell line SKOV-3 (▲) and the human cervical carcinoma cell line Ca Ski (●), where cellular viability is analyzed by MTT assay.

In accordance with an aspect of the present invention, there is provided an anticancer composition comprising citric acid as an active component.

The above anticancer composition is characterized by comprising citric acid as an active component at an amount of 0.1–10 wt. % of total weight of the composition, preferably 0.5–5 wt. %, and a pharmaceutically acceptable carrier. The carrier used in the anticancer composition includes the commonly used carriers, adjuvants and vehicles in the pharmaceutical field.

In accordance with another aspect of the present invention, there is provided an anticancer composition comprising citric acid and zinc as active components.

The above anticancer composition is characterized by comprising as active components citric acid at an amount of 0.1–10 wt. % of total weight of the composition, preferably 0.5–5 wt. %, zinc at an amount of 0.01–5 wt. % of total weight of the composition, preferably 0.1–1 wt. %, and a pharmaceutically acceptable carrier. The carrier used in the anticancer composition includes the commonly used carriers, adjuvants and vehicles in the pharmaceutical field.

In accordance with a further aspect of the present invention, there is provided an anticancer composition comprising citric acid and albumin as active components.

The above anticancer composition is characterized by comprising as active components citric acid at an amount of 0.1–10 wt. % of total weight of the composition, preferably 0.5–5 wt. %, albumin at an amount of 0.01–5 wt. % of total weight of the composition, preferably 0.1–1 wt. %, and a pharmaceutically acceptable carrier. The carrier used in the anticancer composition includes the commonly used carriers, adjuvants and vehicles in the pharmaceutical field.

In accordance with a still further aspect of the present invention, there is provided an anticancer composition comprising citric acid, zinc and albumin as active components.

The above anticancer composition is characterized by comprising as active components citric acid at an amount of 0.1–10 wt. % of total weight of the composition, preferably 0.5–5 wt. %, zinc at an amount of 0.01–5 wt. % of total weight of the composition, preferably 0.1–1 wt. %, albumin at an amount of 0.01–5 wt. % of total weight of the composition, preferably 0.05–1 wt. %, and a pharmaceutically acceptable carrier. The carrier used in the anticancer composition includes the commonly used carriers, adjuvants and vehicles in the pharmaceutical field.

Citric acid; zinc; and albumin, selectively used as an active component in each aspect, may be used in the anticancer compositions of the present invention in the following forms, but the present invention is not limited to them.

Citric acid useful in the present invention may be in any of the forms extracted from seeds or fruit juice of a variety of plants, where citric acid exists in a free form. In addition, citric acid prepared by a surface fermentation process or submerged fermentation process using the fungus *Aspergillus niger* may be used in the anticancer compositions of the present invention. In the process of preparing citric acid, fermentation is performed using molasses as an energy source, and various centrifugal separators, including a separator with self-cleaning bowl, a separator with nozzle bowl and a screw decanter, are used.

Zinc useful in the present invention may be in any of the forms extracted from oysters, crustaceans, fishes, animal products such as red meat, and various vegetable products including grain, beans, nuts and seeds, in which zinc is present in abundance. Zinc may be used in various forms in the anticancer compositions of the present invention. Zinc sulfate has been used in most clinical trials, but zinc ions in other forms are also easily absorbed and utilized by the body. Examples of the available forms of zinc include chelated zinc ions with picolinate, acetate, sodium citrate, glycerate and monomethionine.

Albumin useful in the present invention may include animal albumin, which are exemplified by egg ovalbumin, human serum albumin, lactoalbumin of milk and myogen, and vegetable albumin, which are exemplified by leucosin of wheat, legumelin of peas, and ricin of castor oil. The preferred albumin is human serum albumin, commonly used for medical purposes. Human serum albumin may be prepared by directly isolating and purifying albumin from blood, using a bacterial expression system based on genetic engineering techniques (Goodey A. R. TIBTECH, 1993, Vol. 11, p 430.), and using an eukaryotic cell (e.g., yeast) as a host for production of recombinant albumin (Sleep et al. Bio/Technology 8, 1990, p 42; Okabayashi et al. J. Biochem., 1991, Vol. 110, p 103; Kang et al. J. Microbiol. Biotechnol., 1998, Vol. 8, p 42; Fleer et al. Bio/Technology 9, 1991, p 968–75.).

The anticancer composition according to the present invention has activity of stimulating cell death of tumor cells or inhibiting proliferation of tumor cells by inducing apoptosis of tumor cells. In contrast to necrosis, meaning pathological cell death, apoptosis is a programmed cell death under inherent genetic control, and is induced according to an encoded program by apoptosis-related genes activated by specific external or internal factors. Activation of apoptosis-inducing genes results in biosynthesis or degradation of translation products of programmed cell death genes, eventually causing cell death. Apoptosis is typically evaluated by a biochemical method investigating DNA fragmentation, or a molecular biological method detecting expression of apoptosis-associated proteins. According to a large number of recent reports, it was demonstrated that substances inducing apoptosis in tumor cells control cell death of tumor cells, and effectively suppress diverse cancers.

Figure 7:
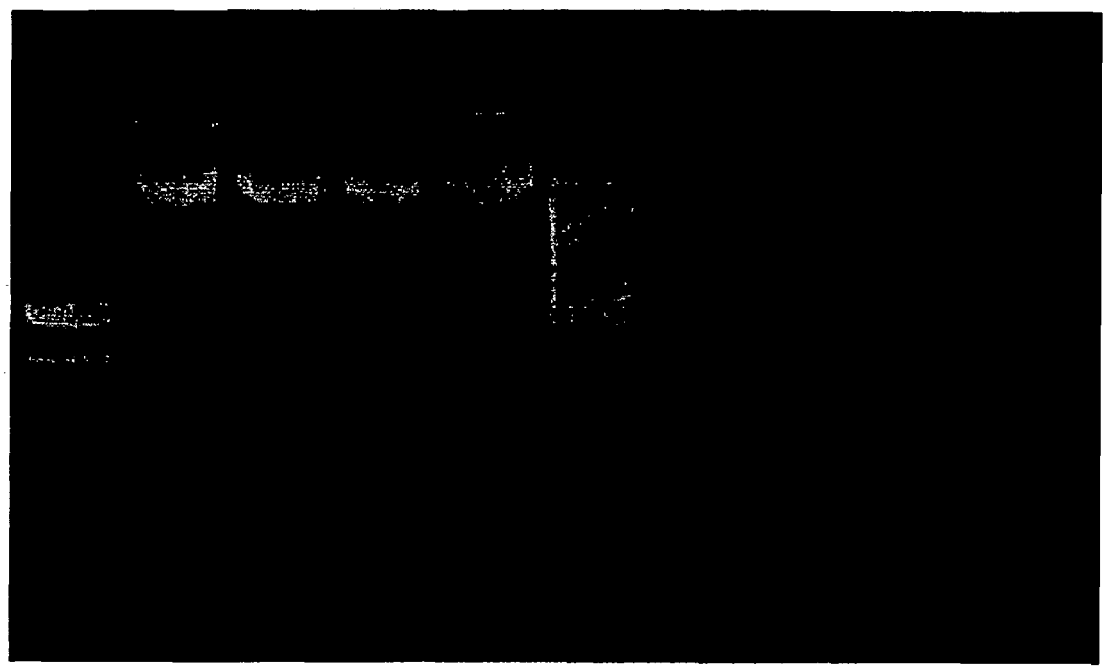
FIG. 7 is a photograph showing a result of electrophoresis on an agarose gel of DNA extracted from the human ovarian adenocarcinoma cell line SKOV-3 treated with an anticancer composition comprising citric acid, zinc and albumin as active components according to the present invention.
Figure 8:
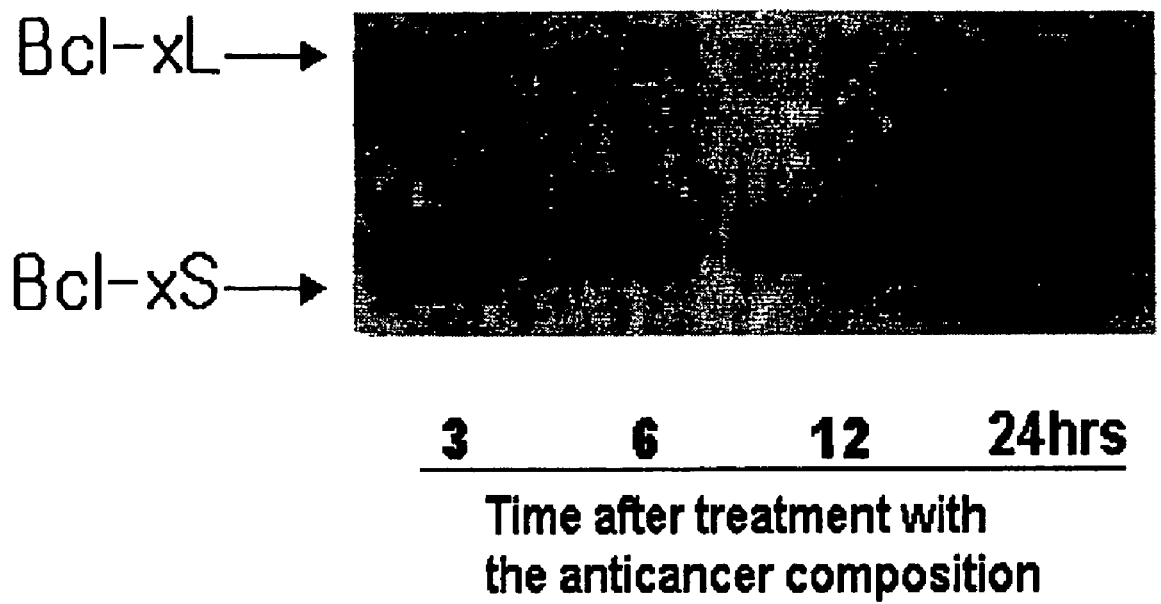
FIG. 8 is a photograph showing expression of Bcl-xL and Bcl-xS proteins in the human ovarian adenocarcinoma cell line SKOV-3 treated with an anticancer composition comprising citric acid, zinc and albumin as active components according to the present invention by immunoblotting.
Figure 9:
FIG. 9 is a photograph showing expression of phospho-Erk protein in the human ovarian adenocarcinoma cell line SKOV-3 treated with an anticancer composition comprising citric acid, zinc and albumin as active components according to the present invention by immunoblotting.

In the present invention, the aforementioned methods are used to verify that the mechanism of cell death specifically induced by the anticancer composition of the present invention is apoptosis. That is, DNA fragmentation was found in DNA samples extracted from tumor cells treated with the anticancer composition of the present invention (FIG. 7). In addition, apoptosis-associated proteins were detected in tumor cells treated with the anticancer composition of the present invention (FIGS. 8 and 9). The apoptosis-associated proteins identified to be expressed by the anticancer composition of the present invention are Bcl (B cell lymphoma)-xL, Bcl-xS and phospho-Erk. Bcl-xL and Bcl-xS proteins belong to the Bcl-2 family. Bcl-xL protein serves as an important suppressor of apoptosis, and Bcl-xS protein, in contrast to Bcl-xL, activates apoptosis (Arriola et al. Oncogene, 1999, Vol. 18, p 1457; and Shimizu et al. Nature, 1995, Vol. 374, p 811.). On the other hand, phospho-Erk (phosphorylation extracellular signal-regulated kinases) participates in cellular proliferation via a phosphorylation process. Phospho-Erk expression is reduced during apoptosis, indicating that stoppage of cellular proliferation induces apoptosis in cells (Rachel et al. Experimental Cell Research, 2001, Vol. 268, p 84.).

Owing to its anticancer effect of inducing apoptosis in tumor cells, it will be apparent to those skilled in the art that the anticancer composition of the present invention, applied to epithelial ovarian cancer as an illustrative cancer type in the present invention, is applicable to other types of cancer.

Therefore, the anticancer composition of the present invention may be useful for treatment of the following cancer types, but is not limited to them: bladder, breast, intestine, kidney, liver, lung (including small cell lung carcinoma), brain, esophagus, gallbladder, ovary, pancreas, stomach, cervical, thyroid, prostate and skin (including squamous cell carcinoma) carcinomas; hematopoietic tumors in the lymphatic system including leukemia, acute lymphoid leukemia, acute lymphoblastic leukemia, B-cell lymphoma, T-cell lymphoma, Hodgkin's lymphoma, non-Hodgkin's lymphoma, hairy cell lymphoma and Burkitt's lymphoma; hematopoietic tumors in the bone marrow including acute and chronic myelogenous leukemia, myelodysplastic syndrome and promyelocytic leukemia; tumors originating from mesenchyme, including fibrosarcoma and rhabdomyosarcoma; tumors in the central and peripheral nervous systems, including astrocytoma, neuroblastoma, glioma and schwanoma; and other tumors including melanoma, seminoma, teratoma, osteosarcoma, xeroderma pigmentosum, keratoacanthoma, thyroid follicular carcinoma and Kaposi's sarcoma.

In a preferred aspect, the anticancer composition of the present invention is useful for suppression or treatment of lung cancer, brain cancer, breast cancer, large intestine cancer, pregnancy choriocarcinoma and epithelial ovarian cancer, and particularly preferably epithelial ovarian cancer.

The carrier useful in the anticancer composition of the present invention includes the commonly used carriers, adjuvants and vehicles, in the pharmaceutical field, which are as a whole called "pharmaceutically acceptable carriers".

Non-limiting pharmaceutically acceptable carriers useful in the anticancer composition of the present invention include ion exchange, alumina, aluminum stearate, lecithin, serum proteins, buffering agents (e.g., sodium phosphate, glycine, sorbic acid, potassium sorbate, partial glyceride mixtures of vegetable saturated fatty acids), water, salts or electrolytes (e.g., protamine sulfate, disodium hydrophosphate, potassium hydrophoshate, sodium chloride, and zinc salts), colloidal silica, magnesium trisilicate, polyvinylpyrrolidone, cellulose-based substrates, polyethylene glycol, sodium carboxymethylcellulose, polyarylate, waxes, polyethylene-polyoxypropylene-block copolymers, polyethylene glycol, and wool fat.

The anticancer composition of the present invention may be administered via any of the common routes, if being able to reach the desired tissue. Therefore, the anticancer composition may be administered topically, orally, parenterally, intraocularly, transdermally, intrarectally and intraluminally, and may be formulated into solutions, suspensions, tablets, pills, capsules and sustained release preparations. The term "parenteral", as used herein, includes subcutaneous, intranasal, intravenous, intraperitoneal, intramuscular, intra-articular, intra-synovial, intrasternal, intracardial, intrathecal, intralesional and intracranial injection or infusion techniques.

In an aspect, when formulated as a solid preparation for oral application, the anticancer composition of the present invention may include, in addition to the active ingredient, diluents (e.g., lactose, dextrose, sucrose, cellulose, corn starch or potato starch), lubricants (e.g., silica, talc, stearic acid, magnesium or calcium stearate, and/or polyethylene glycol), binders (e.g., starch, gum arabic, gelatin methylcellulose, carboxymethylcellulose or polyvinyl pyrrolidone), disintegrators (e.g., starch, alginic acid, alginate or sodium starch glycolate), formal mixtures, dyes, sweetening agents, humectants (e.g., lecithin, polysorbate, laurylsulfate), and the commonly used, pharmaceutically inert substances. The solid formulation for oral administration may be prepared by the methods known in the art, for example, via a process comprising mixing, granulation, tableting and sugar-coating or film-coating.

In another aspect, when formulated as liquid compositions for oral application, such as solutions, emulsions, suspensions, syrups or elixirs, the anticancer composition of the present invention may include the commonly used inert diluents (e.g., purified water, ethanol). If desired, the liquid composition may further include adjuvants, for example, humectants and emulsifiers, sweetening agents, perfumes, aromatic agents, and antiseptic agents.

In a further aspect, the anticancer composition of the present invention may be formulated as aqueous solutions for parenteral administration. Preferably, a suitable buffer solution, such as Hank's solution, Ringer's solution or physiologically buffered saline, may be employed. Aqueous injection suspensions may be supplemented with substances capable of increasing viscosity of the suspensions, which are exemplified by sodium carboxymethylcellulose, sorbitol and dextran. In addition, suspensions of the active components, such as oily injection suspension, include lipophilic solvents or carriers, which are exemplified by fatty oils such as sesame oil, and synthetic fatty acid esters such as ethyl oleate, triglycerides or liposomes. Polycationic non-lipid amino polymers may be also used as vehicles. Optionally, the suspensions may contain suitable stabilizers or drugs to increase solubility of components and obtain high concentration of the components.

The anticancer composition of the present invention is preferably in the form of a sterile injectable preparation, such as a sterile injectable aqueous or oleaginous suspension. Such suspension may be formulated according to the methods known in the art, using suitable dispersing or wetting agents (e.g., Tween 80) and suspending agents. The sterile injectable preparations may also be a sterile injectable solution or suspension in a non-toxic parenterally-acceptable diluent or solvent, such as a solution in 1,3-butanediol. The acceptable vehicles and solvents include mannitol, water, Ringer's solution and isotonic sodium chloride solution. In addition, sterile fixed oils may conventionally be employed as a solvent or suspending medium. For this purpose, any bland fixed oil may be employed, including synthetic mono- or diglycerides. In addition, fatty acids, such as oleic acid and glyceride derivatives thereof, may be used in the preparation of injectable preparations, likewise the pharmaceutically acceptable natural oils (e.g., olive oil or castor oil), and particularly, polyoxyethylated derivatives thereof.

The aforementioned aqueous composition is sterilized mainly by filtration using a filter to remove bacteria, mixing with disinfectants or in combination with radiation. The sterilized composition can be hardened, for example, by freeze-drying to obtain a hardened product, and for practical use, the hardened composition is dissolved in sterilized water or a sterilized diluted solution.

The term "therapeutically effective amount", as used herein in connection with the anticancer composition of the present invention, means an amount at which an active component shows improved or therapeutic effect toward a cancer type treated with the anticancer composition of the present invention. The therapeutically effective amount of the anticancer composition of the present invention may vary according to patient's age and sex, application sites, administration frequency, administration duration, formulation type and adjuvant types. Typically, daily dosage is, in case of injection preparations, 1–500 mg, preferably, 50–200 mg, and most preferably, 100–150 mg, and administered over 1 to 5 times. In case of orally administered preparations, daily dosage is typically 1–2,000 mg, preferably, 250–1,000 mg, and most preferably, 300–500 mg, and administered over 1 to 5 times.

The present invention will be explained in more detail with reference to the following an example in conjunction with the accompanying drawings. However, the following example is provided only to illustrate the present invention, and the present invention is not limited to the example.

EXAMPLE 1

Preparation of Injection Preparations

Anticancer compositions according to the present invention, comprising various combinations of active components, were prepared as follows. Citric acid (Sigma, USA), zinc (Sigma, USA), and albumin (Sigma, USA) were selectively mixed according to the mixing ratios in Table 1, below, and each of the mixtures was dissolved in sterilized water. The resulting mixture was adjusted to pH 7.0 using 10 N NaOH, and then filled into a vial (100 mg).

TABLE 1

Contents (wt. %) of active components of anticancer compositions

| Anticancer composition | Citric acid | Zinc | Albumin |
|---|---|---|---|
| 1 | 4 | 0 | 0 |
| 2 | 4 | 0.4 | 0 |
| 3 | 4 | 0 | 0.8 |
| 4 | 4 | 0.4 | 0.8 |

EXAMPLE 2

Preparation of Tablets

Citric acid (Sigma, USA), zinc (Sigma, USA), and albumin (Sigma, USA) were selectively mixed according to the mixing ratios in Table 1, above, and each of the mixtures was mixed with 30 wt. % of lactose, 5 wt. % of magnesium stearate, 10 wt. % of sodium starch glycolate, and sterilized water. The resulting mixture was adjusted to pH 7.0 using 10 N NaOH, incubated at 30–60° C. for 1 hr with stirring, and cooled to room temperature. Thereafter, the mixture was tableted according to the conventional methods, thereby producing tablets each containing 350 mg of the powdered mixture.

EXAMPLE 3

Evaluation of Effects of Anticancer Composition Comprising Citric Acid as an Active Component on Viability of Tumor Cells The anticancer composition comprising citric acid as an active component was evaluated for its effect on growth and survival of tumor cells, by preparing several compositions comprising various concentrations of citric acid according to Table 2, below, treating tumor cells with the compositions, and investigating cellular viability. SKOV-3 cells (human ovarian adenocarcinoma cell line, ATCC No. HTB-77) and Ca Ski cells (human cervical carcinoma cell line, ATCC No. CRL-1550) were used.

SKOV-3 and Ca Ski cells were plated onto 96-well plates at a density of $3 \times 10^3$ cells, and cultured for 12 hrs in DMEM (Dulbecco's modified Eagle's medium, Life Technology, Inc., U.S.A.) supplemented with 10% (v/v) FBS (fetal bovine serum), 100 µg/ml of streptomycin, 100 U/ml of penicillin and 100 µg/ml of L-glutamine.

The cultured cells were treated with the compositions comprising various concentrations of citric acid, which were prepared according to the same method as in Example 1, and incubated at 37° C. under 5% $CO_2$ for 24 hrs. Thereafter, cellular viability was evaluated.

TABLE 2

Contents (wt. %) of citric acid of the compositions

| | Composition No. | | | | | | |
|---|---|---|---|---|---|---|---|
| | Control | 1 | 2 | 3 | 4 | 5 | 6 | 7 |
| Conc. of citric acid | 0 | 0.2 | 0.4 | 0.8 | 1 | 1.5 | 2 | 4 |

Cellular viability was analyzed by the known MTT (3-(4,5 dimethylthiazol-2-yl)-2,5-2H-tetrazolium bromide) assay (Hansen, M. B. et al., J. Immunol. Methods, 1986, 172, p 203–10.). 20 µl of an MTT solution (10 mg/ml of MTT in PBS (phosphate buffered saline) was added to each well, and the plates were incubated at 37° C. for 4 hrs. After removing the culture medium, formazan crystal dissolved in 200 µl of DMSO (dimethyl sulfoxide) was added to each well, followed by incubation at room temperature for 10 min with agitation. Absorbance was measured at 540 nm using a Bio-Rad model 3550 microplate reader (Richmond, Calif.). Herein, the cells not treated with the composition comprising citric acid were used as a control. The results are given in FIG. 1.

As shown in FIG. 1, when treating the tumor cell lines SKOV-3 (▲) and Ca Ski (●) with the compositions comprising citric acid as an active component, cellular viability was found to decrease in a manner inversely dependent on concentration of the active component, citric acid. In particular, in case of being treated with the compositions containing over 0.4 wt. % of citric acid, viability of the tumor cells was reduced to below 50%, while being reduced to below 20% in case of being treated with the compositions containing over 1 wt. % of citric acid.

EXAMPLE 4

Evaluation of Effects of Anticancer Composition Comprising Citric Acid and Zinc as Active Components on Viability of Tumor Cells The anticancer composition comprising citric acid and zinc as active components was evaluated for its effects on growth and survival of tumor cells, by preparing several compositions comprising various concentrations of citric acid and zinc according to Table 3, below, treating tumor cells with the compositions, and investigating cellular viability. SKOV-3 and Ca Ski cell lines were used. Cell culture, treatment of the tumor cells with the compositions and cellular viability analysis were performed according to the same method as in Example 3.

TABLE 3

Contents (wt. %) of citric acid and zinc of the compositions

| | Composition No. | | | | | | |
|---|---|---|---|---|---|---|---|
| | Control | 1 | 2 | 3 | 4 | 5 | 6 | 7 |
| Conc. of citric acid | 0 | 0.2 | 0.4 | 0.8 | 1 | 1.5 | 2 | 4 |
| Conc. of zinc | 0 | 0.02 | 0.04 | 0.08 | 0.1 | 0.15 | 0.2 | 0.4 |

Figure 2:
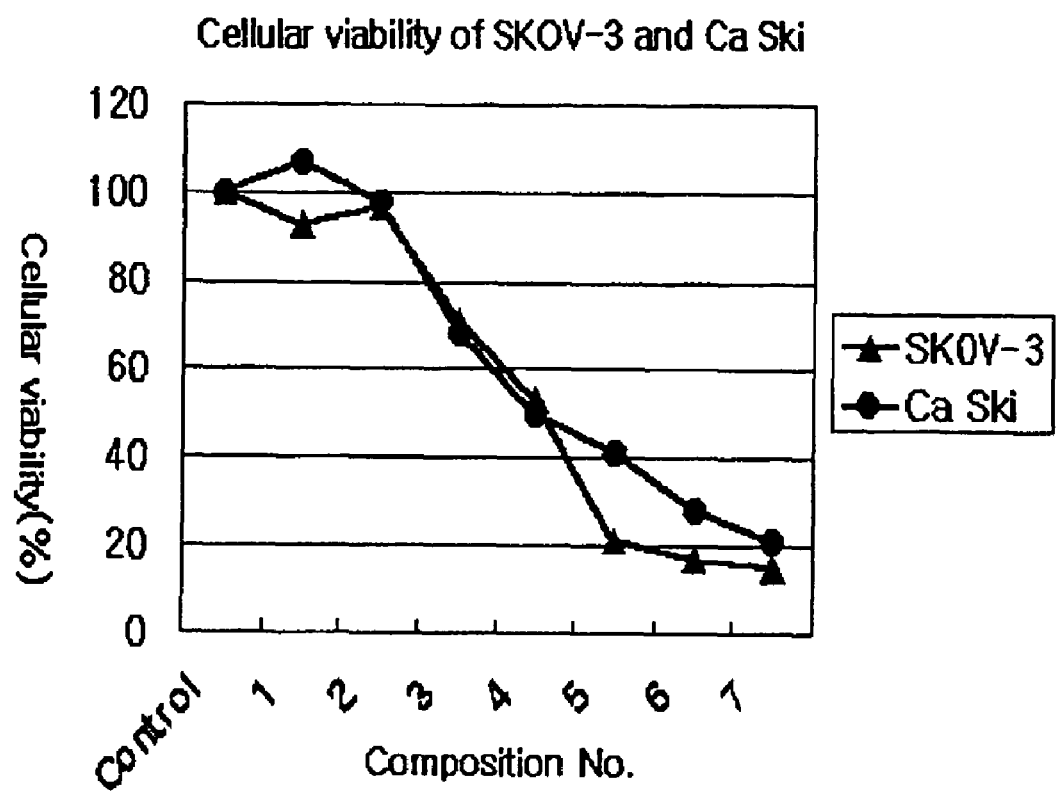
FIG. 2 is a graph showing effects of an anticancer composition comprising citric acid and zinc as active components according to the present invention on viability of the human ovarian adenocarcinoma cell line SKOV-3 (▲) and the human cervical carcinoma cell line Ca Ski (●), where cellular viability is analyzed by MTT assay.

As shown in FIG. 2, when treating the tumor cell lines SKOV-3 (▲) and Ca Ski (●) with the compositions comprising citric acid and zinc as active components, cellular viability was found to decrease in a manner inversely dependent on concentration of the active components, citric acid and zinc. In particular, in case of being treated with the composition 4, viability of the tumor cells were reduced to below 60%, while being reduced to below 30% in case of being treated with the composition 6.

EXAMPLE 5

Evaluation of Effects of Anticancer Composition Comprising Citric Acid and Albumin as Active Components on Viability of Tumor Cells The anticancer composition comprising citric acid and albumin as active components was evaluated for its effects on growth and survival of tumor cells, by preparing several compositions comprising various concentrations of citric acid and albumin according to Table 4, below, treating tumor cells with the compositions, and investigating cellular viability. SKOV-3 and Ca Ski cell lines were used. Cell culture, treatment of the tumor cells with the compositions and cellular viability analysis were performed according to the same method as in Example 3.

TABLE 4

Contents (wt. %) of citric acid and albumin of the compositions

| | Composition No. | | | | | | | |
|---|---|---|---|---|---|---|---|---|
| | Control | 1 | 2 | 3 | 4 | 5 | 6 | 7 |
| Conc. of citric acid | 0 | 0.2 | 0.4 | 0.8 | 1 | 1.5 | 2 | 4 |
| Conc. of albumin | 0 | 0.04 | 0.08 | 0.16 | 0.2 | 0.3 | 0.4 | 0.8 |

Figure 3:
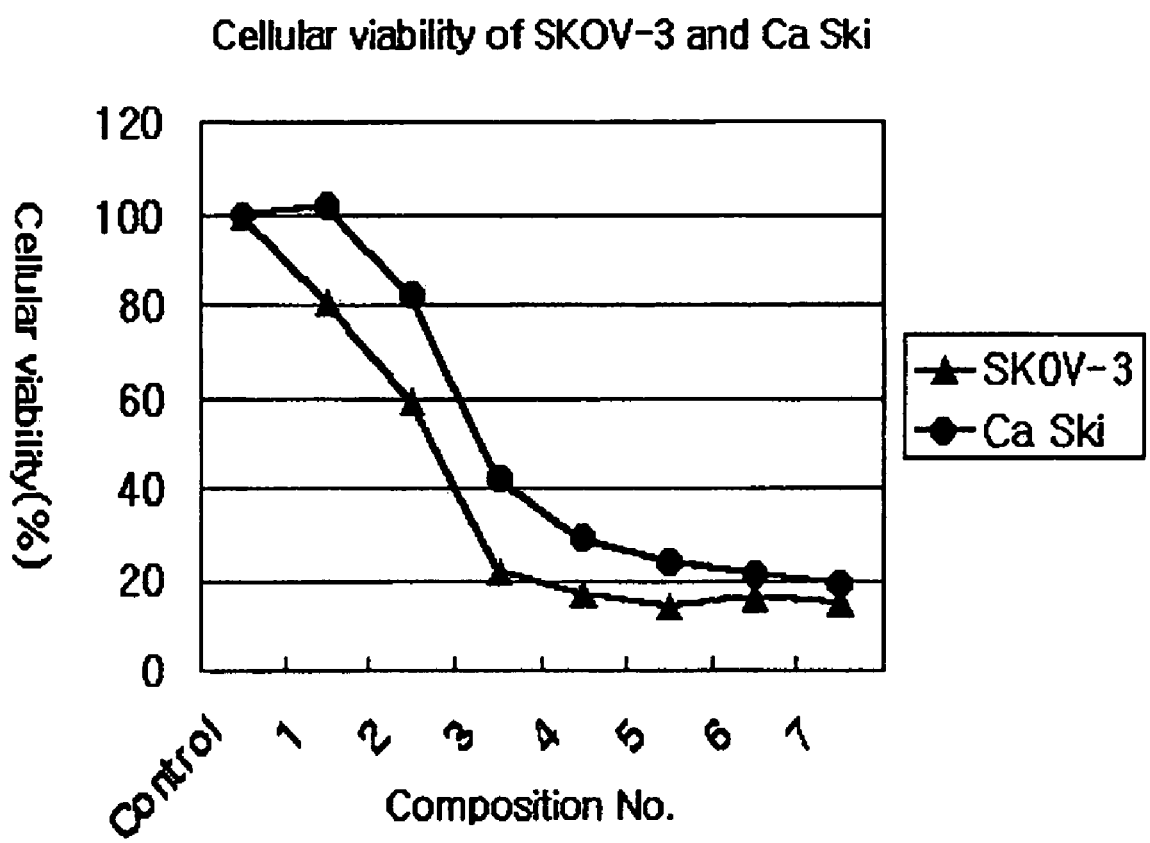
FIG. 3 is a graph showing effects of an anticancer composition comprising citric acid and albumin as active components according to the present invention on viability of the human ovarian adenocarcinoma cell line SKOV-3 (▲) and the human cervical carcinoma cell line Ca Ski (●), where cellular viability is analyzed by MTT assay.

As shown in FIG. 3, when treating the tumor cell lines SKOV-3 (▲) and Ca Ski (●) with the compositions comprising citric acid and albumin as active components, cellular viability was found to decrease in a manner inversely dependent on concentration of the active components citric acid and albumin. In particular, in case of being treated with the composition 3, viability of the tumor cells were reduced to below 40%, while being reduced to below 20% in case of being treated with the composition 6.

EXAMPLE 6

Evaluation of Effect of Anticancer Composition Comprising Citric acid, Zinc and Albumin as Active Components on Viability of Tumor Cells The anticancer composition comprising citric acid, zinc and albumin as active components was evaluated for its effect on growth and survival of tumor cells, by preparing several compositions comprising various concentrations of citric acid, zinc and albumin according to Table 5, below, treating tumor cells with the compositions, and investigating cellular viability. SKOV-3, NIH:OVCAR-3 (human ovarian adenocarcinoma cell line, ATCC No. HTB-161) and WI 38 (normal human lung fibroblast cell line, ATCC No. CCL-75) cells were used. Cell culture, treatment of the cells with the compositions and cellular viability analysis were performed according to the same method as in Example 3.

TABLE 5

Contents (wt. %) of citric acid, zinc and albumin of the compositions

| | Composition No. | | | | | | | |
|---|---|---|---|---|---|---|---|---|
| | Control | 1 | 2 | 3 | 4 | 5 | 6 | 7 |
| Conc. of citric acid | 0 | 0.2 | 0.4 | 0.8 | 1 | 1.5 | 2 | 4 |
| Conc. of zinc | 0 | 0.02 | 0.04 | 0.08 | 0.1 | 0.15 | 0.2 | 0.4 |
| Conc. of albumin | 0 | 0.04 | 0.08 | 0.16 | 0.2 | 0.3 | 0.4 | 0.8 |

Figure 4:
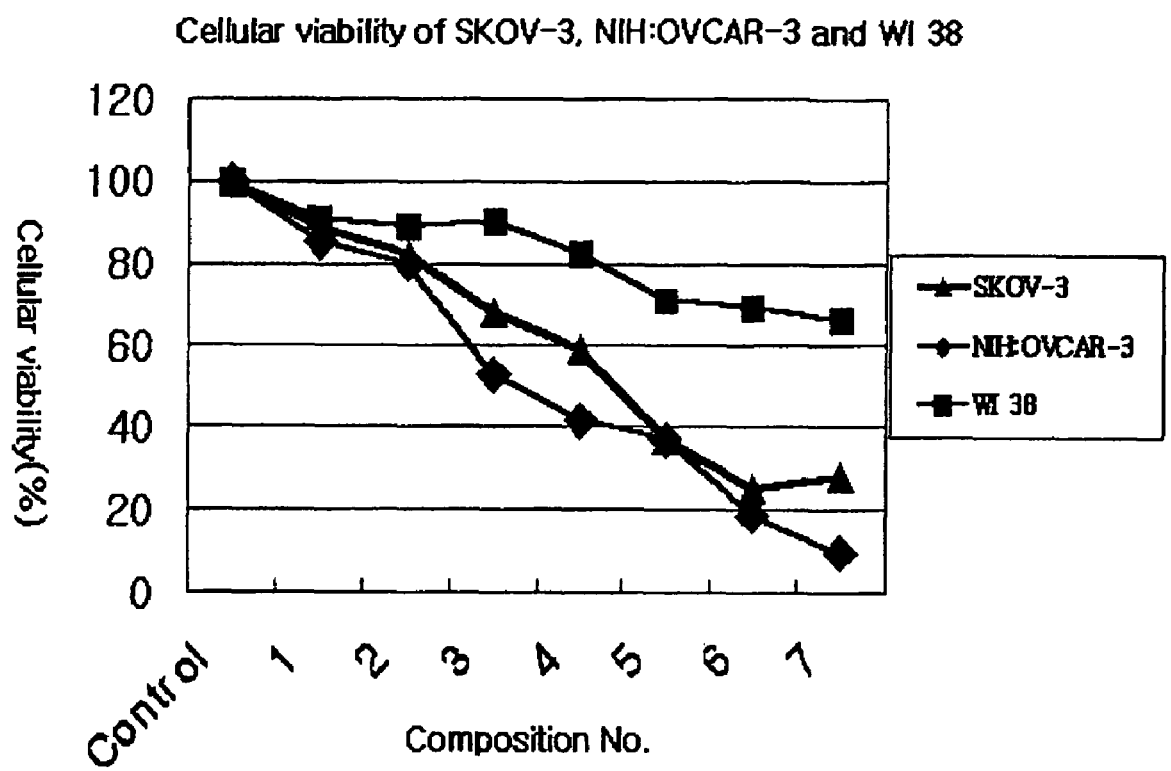
FIG. 4 is a graph showing effects of an anticancer composition comprising citric acid, zinc and albumin as active components according to the present invention on viability of the normal human lung fibroblast cell line WI 38 (■), the human ovarian adenocarcinoma cell line NIH:OVCAR-3 (♦) and the human ovarian adenocarcinoma cell line SKOV-3 (▲), where cellular viability is analyzed by MTT assay.

As shown in FIG. 4, when treating SKOV-3 (▲), NIH:OVCAR-3 (♦) and WI 38 (■) cells with the compositions comprising citric acid, zinc and albumin as active components, viability of the tumor cells was found to decrease in a manner inversely dependent on concentration of the active components citric acid, zinc and albumin, and the normal cell line did not show specific change in cellular viability. In particular, in case of being treated with the composition 5, viability of the tumor cell lines SKOV-3 and NIH:OVCAR-3 were reduced to below 40%, while being reduced to below 20% in case of being treated with the composition 6. In contrast, when treating the normal cell line WI 38 with the compositions as described above, cellular viability was found to remain over 50%. These results indicate that the compositions acts in a tumor cell-specific manner, resulting in cell death of tumor cells.

EXAMPLE 7

Comparison of Effects of the Anticancer Compositions on Viability of Normal Cells with the Known Anticancer Agent TAXOL The normal cell line 293 (human kidney epithelial cell line, ATCC No. CRL-1573) was treated with the anticancer composition of the present invention (the anticancer composition 4 of Table 1), prepared in Example 1, and the known anticancer agent TAXOL, and their effects on cell growth and survival were evaluated. Cell culture, treatment of the cells with the composition 4 prepared in Example 1 and TAXOL, and cellular viability analysis were performed according to the same method as in Example 3.

Figure 5:
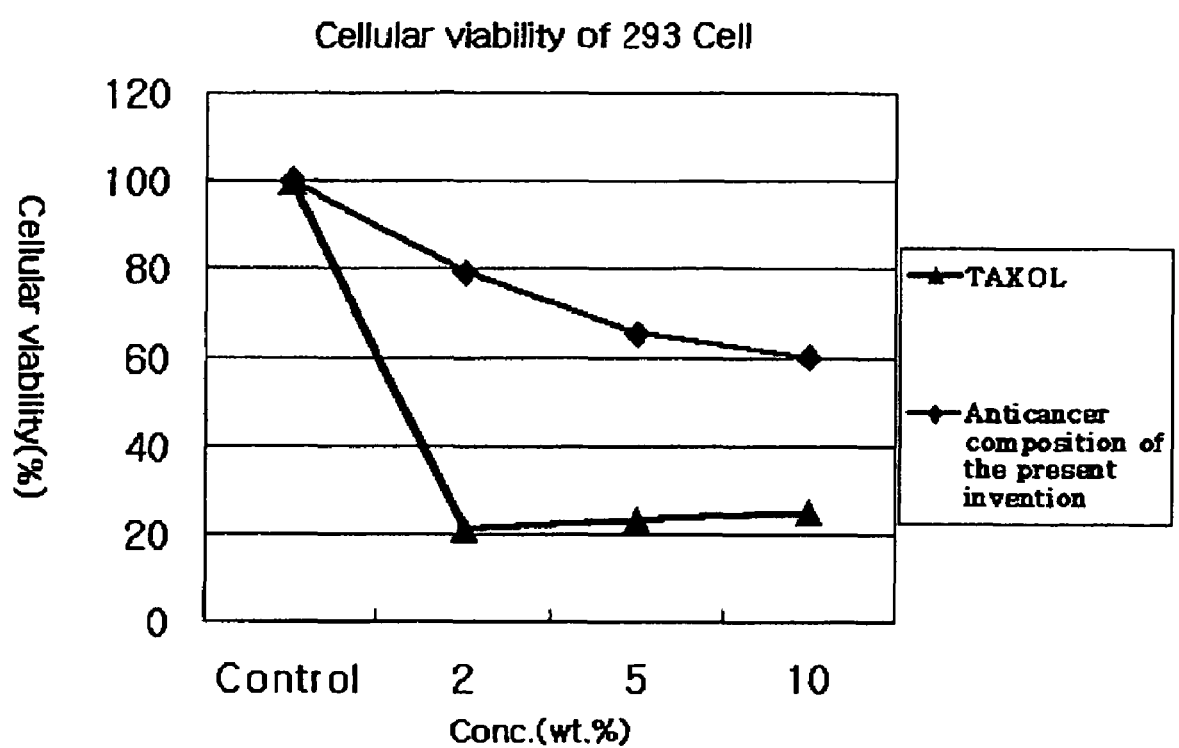
FIG. 5 is a graph showing effects of an anticancer composition comprising citric acid, zinc and albumin as active components according to the present invention (●), and the known anticancer agent TAXOL (▲) on viability of the human kidney epithelial cell line 293, where cellular viability is analyzed by MTT assay.

As shown in FIG. 5, when treating 293 cells with the anticancer composition of the present invention (●), cellular viability was about 60%. In contrast, when treated with TAXOL (▲), 293 cells showed viability of about 20–25%. These results demonstrate that the anticancer composition of the present invention has much lower cytotoxicity toward normal cells, and thus is superior to the conventional anticancer agent TAXOL.

EXAMPLE 8

Flow Cytometric Analysis of Cells Treated with the Anticancer Composition of the Present Invention The anticancer composition of the present invention, prepared in Example 1, was evaluated for effect on DNA division by flow cytometry.

WI 38, NIH:OVCAR-3 and SK-OV-3 cells were plated onto 96-well plates at a density of $2 \times 10^6$ cells, 100 ml of the anticancer composition prepared in Example 1 (the anticancer composition 4 of Table 1) was added to each well, and the plates were incubated for 6 hrs and 24 hrs according to the same method as in Example 3. A control was not treated with the anticancer composition. Cells were harvested, and washed with pre-cooled PBS twice. The washed cells were fixed with 100% ethanol at 4° C. for 24 hrs. The resulting cells were suspended in 500 µl of PBS, treated with 20 µg/ml of RNase at 37° C. for 30 min, and cooled on ice for 10 min. The resulting isolated DNA was stained with 50 µg/µl of PI (propidium iodide), and DNA division was analyzed using a flow cytometer (Becton Dickinson FACS system, U.S.A.). Herein, propidium fluorescence was developed using a cooled 15 mW argon ion laser, and emitted light was collected using a 617 long pass optical filter. DNA Modeling was determined by ModFit software (ModFit, Verity Software House, Topsham, Me., U.S.A.).

Figure 6:
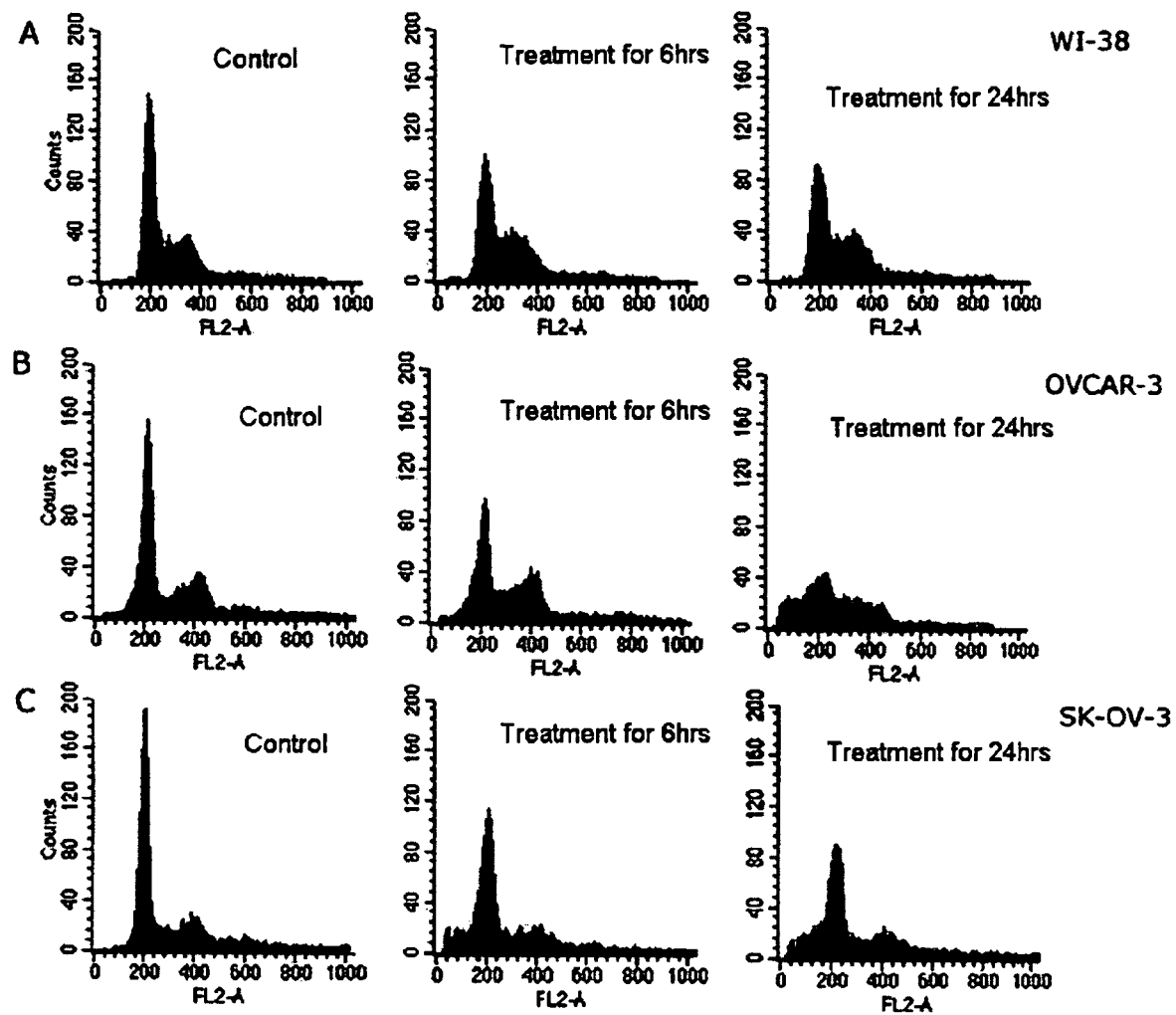
FIG. 6 is a result of flow cytometric analysis showing effects of an anticancer composition comprising citric acid, zinc and albumin as active components according to the present invention on cell cycle of the normal human lung fibroblast cell line WI 38 (A), the human ovarian adenocarcinoma cell line NIH:OVCAR-3 (B) and the human ovarian adenocarcinoma cell line SKOV-3 (C).

As shown in FIG. 6, in WI 38 cell line(A) treated with the anticancer composition of the present invention, the percentage of cells was reduced in the peak of $G_1$ phase (preparation for DNA synthesis), while being gradually increased in the peak of $G_2$ phase (preparation for cell division) with the passage of time. These results indicate that the anticancer composition of the present invention does not influence differentiation and growth of WI 38cells. On the other hand, the cell lines NIH:OVCAR-3 (B) and SKOV-3 (C) were arrested at the $G_1$ phase. In addition, cells were accumulated in the $G_0$–$G_1$ (sub-$G_1$ fraction) phase, while cell population was significantly reduced in the cell cycle phases S (DNA synthesis) and G2-M (mitosis), indicating induction of apoptosis.

EXAMPLE 9

DNA Laddering Assay of Cells Treated with the Anticancer Composition of the Present Invention DNA laddering assay was performed to investigate the mechanism of cell death induced by the anticancer composition of the present invention, observed in Example 8. SKOV-3 cells were plated onto 96-well plates at a density of $2 \times 10^6$ cells, 100 ml of the anticancer composition prepared in Example 1 (the anticancer composition 4 of Table 1) was added to each well, and the plates were incubated for 2, 4, 6, 12, 24, 48, 72 and 96 hrs according to the same method as in Example 3. Cells were harvested after each incubation, and DNA was then isolated by the conventionally known method, as follows (Leszczynski D. et. al. Photochem. Photobiol., 1996, Vol. 64, p 936.). The harvested cells were suspended in lysis buffer consisting of 0.5% SDS (sodium-dodecyl-sulfate), 2 mM EDTA (ethylene diamine tetra acetic acid), 100 mg/ml of proteinase K and 50 mM Tris-HCl buffer (pH 8.0), incubated at 55° C. for 3 hrs, and extracted with an equal volume of phenol: chloroform: isoamylalcohol (25:24:1). Then, DNA was precipitated with 0.1 volume of ammonium acetate and 2.5 volume of cool absolute ethanol, followed by incubation at −20° C. overnight. DNA pellet was dissolved in TE buffer (0.5 M EDTA in 1 M Tris-HCl buffer, pH 8.0), and treated with 100 mg/ml of RNase A at 37° C. for 1 hr. The resulting DNA sample was separated on a 1.5% agarose gel containing 0.5 µg/ml of ethidium bromide under 60 V for 1 hr, and exposed to UV.

As shown in FIG. 7, in SKOV-3 cells treated with the anticancer composition of the present invention, about 100-bp DNA ladder was observed 12 and 24 hrs after treatment. Typically, nucleosomes are cleaved at linker regions between nucleosomal units during induction of apoptosis, resulting in production of about 100-bp DNA ladder. These results indicate that the mechanism of cell death induced by the anticancer composition of the present invention is apoptosis.

EXAMPLE 10

Expression Analysis of Apoptosis-Associated Proteins in Cells Treated with the Anticancer Composition of the Present Invention Expression patterns of the apoptosis-associated proteins Bcl-xL, Bcl-xS and phospho-Erk were analyzed to investigate the mechanism of cell death induced by the anticancer composition of the present invention, observed in Example 8.

SKOV-3 cells were plated onto 96-well plates at a density of $2 \times 10^6$ cells, 100 ml of the anticancer composition prepared in Example 1 (the anticancer composition 4 of Table 1) was added to each well, and the plates were incubated for 30 min, 1, 3, 6, 9, 12 and 24 hrs according to the same method as in Example 3. Cells were harvested after each incubation, and lysed with lysis buffer (10 mM Tris, 1 mM EDTA, 1 mM DTT, 1 mM PMSF, protease inhibitor). The resulting cell lysate was subjected to SDS-electrophoresis, and the separated protein was transferred to an ECL nitrocellulose membrane (Amersham Life Science, U.K.). The membrane was then blocked with a blocking solution (5% skim milk in TBST; 10 mM Tris-HCl, pH 8.0. 150 mM NaCl, 0.1% Tween 20) at 4° C. overnight. Thereafter, apoptosis-associated proteins were investigated by immunoblotting analysis, as follows. Primary antibodies to Bcl-xL, Bcl-xS and phospho-Erk were diluted to 1:500 in the blocking solution. The blocked membrane was reacted with the diluted primary antibodies at 4° C. overnight, and then with a 1:5000 dilution of a secondary antibody (goat anti-rabbit IgG-HRP; Santa Cruz Biotechnology, U.S.A.) in the blocking solution at room temperature for 1 hr. After each treatment of primary and secondary antibodies, the membrane was washed three times for 15 min per each washing, and exposed to an ECL Hyperfilm (Amersham Life Science, U.K.).

As shown in FIG. 8, in cells treated with the anticancer composition of the present invention, expression of Bcl-xL protein suppressing apoptosis was gradually reduced with the passage of time. In contrast, Bcl-xS protein inducing apoptosis was increasingly expressed with the passage of time. These results indicate that the mechanism for cell death induced by the anticancer composition of the present invention is apoptosis.

As shown in FIG. 9, phospho-Erk protein expression was found to decrease with the passage of time in cells treated with the anticancer composition of the present invention. This result indicates that the anticancer composition of the present invention suppresses proliferation of tumor cells.

EXAMPLE 11

Apoptosis Determination by DNA Fragmentation Assay in Cells Treated with the Anticancer Composition of the Present Invention To investigate the mechanism of cell death induced by the anticancer composition of the present invention, observed in Example 8, DNA release from cells treated with the anticancer composition of the present invention was measured. DNA release was analyzed by detecting BrdU (5'-bromo-2'-deoxy-uridine)-labeled DNA fragments, released from cells to the culture medium, using a cellular DNA fragmentation ELISA (enzyme-linked immunoabsorbant assay) kit (Boehringer Mannheim, Germany). Herein, cells were cultured in the culture medium containing the thymidine analog BrdU, which incorporates into the genomic DNA. BrdU is known not to influence cell growth and apoptosis.

100 ml of the anticancer composition prepared in Example 1 (the anticancer composition 4 of Table 1) was added to each of BrdU-containing culture media of WI 38, NIH:OVCAR-3 and SKOV-3 cells, and the cells were cultured for 24 hrs according to the same method as in Example 3. After collecting culture supernatant at various time intervals, DNA fragments were captured by anti-DNA antibody immobilized on a Nunc-immuno flat-bottom plate, and detected and quantified using an anti-BrdU antibody-peroxidase conjugate. Optical density was measured at 450 nm, where absorbance at 690 nm was used as a standard.

Figure 10:
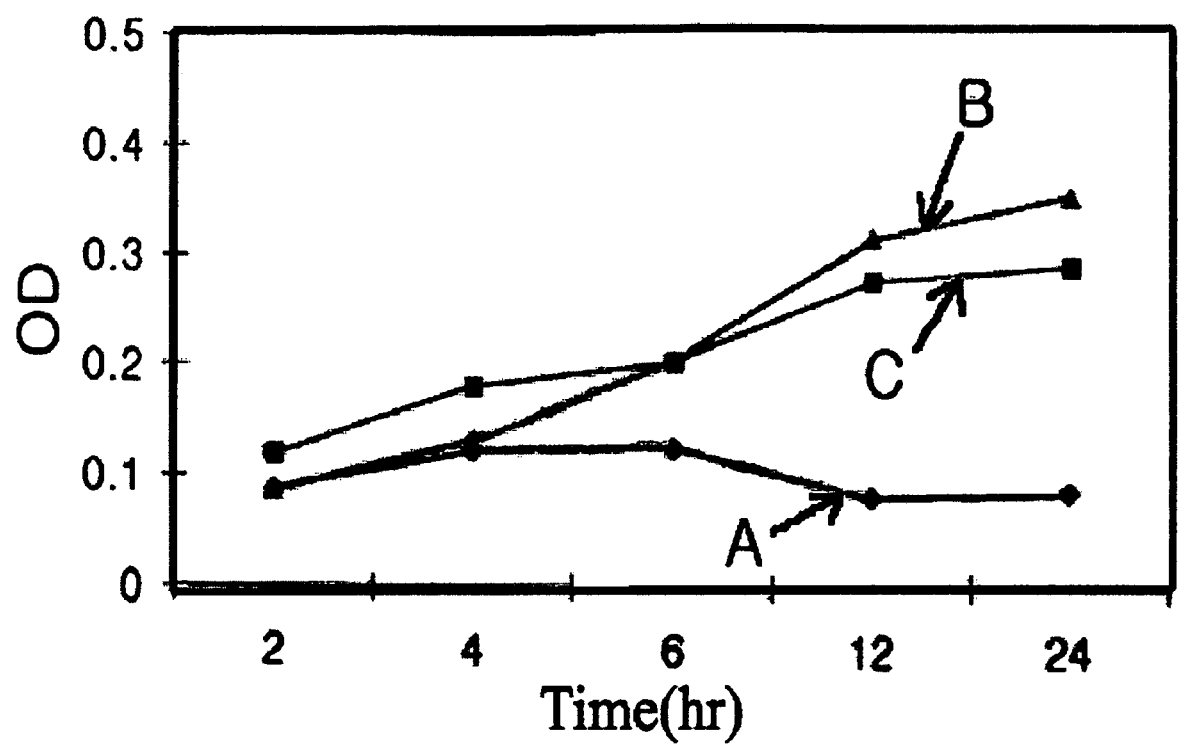
FIG. 10 is a graph showing a result of BrdU test, showing apoptotic effect of an anticancer composition comprising citric acid, zinc and albumin as active components according to the present invention in the normal human lung fibroblast cell line WI 38 (A), the human ovarian adenocarcinoma NIH:OVCAR-3 (B) and the human ovarian adenocarcinoma cell line SKOV-3 (C).

As shown in FIG. 10, in WI 38 cell line (A) treated with the anticancer composition of the present invention, DNA release was not detected, while DNA release was gradually increased with the passage of time in the cell lines NIH: OVCAR-3 (B) and SKOV-3 (C). These results indicate that the anticancer composition of the present invention induce apoptosis in NIH:OVCAR-3 and SKOV-3 cells.

EXAMPLE 12

Nuclear Staining of Cells Treated with the Anticancer Composition of the Present Invention To investigate the mechanism of cell death induced by the anticancer composition of the present invention, observed in Example 8, nuclear staining was performed in cells treated with the anticancer composition of the present invention.

Sterilized cover glasses were placed into 60-mm culture dishes, the human ovarian surface normal epithelial cell line NOSE, NIH:OVCAR-3 cell line and SKOV-3 cell line were plated at a density of $1\times10^4$ cells, and cultured overnight. Thereafter, the cells were treated with 100 ml of the anticancer composition prepared in Example 1 (the anticancer composition 4 of Table 1). After 24 hrs, the cells were washed with PBS twice, and fixed with 3.7% formaldehyde. After washing with PBS three times, the cells were stained with 4 μg/ml of a DAPI (4',6'-diamino-2-phenylinylindole) solution (Sigma, U.S.A.) at room temperature for 10 min. After washing with PBS three times and then distilled water twice, the stained cells fixed on the cover glasses were observed under a fluorescence microscope (Olympus Optical Co., Ltd., U.S.A). The results are given in FIG. 11, in which nuclei were stained in green in non-apoptotic cells, while nuclei of apoptotic cells were stained in red.

Figure 11:
FIG. 11 is a photograph showing DAPI-stained nuclei of the human ovarian surface normal epithelial cell line NOSE, the human ovarian adenocarcinoma NIH:OVCAR-3 and the human ovarian adenocarcinoma cell line SKOV-3, treated with an anticancer composition comprising citric acid, zinc and albumin as active components according to the present invention (green: nuclei of non-apoptotic cells; and red: nuclei of apoptotic cells).
Figure 11:
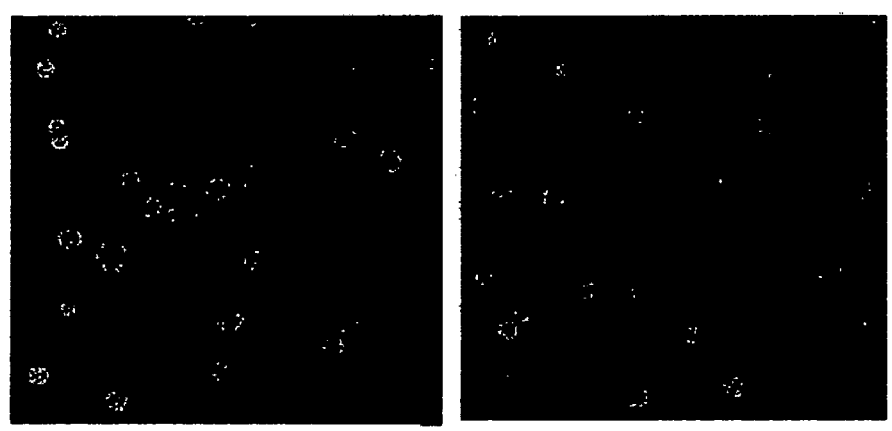
Figure 11:
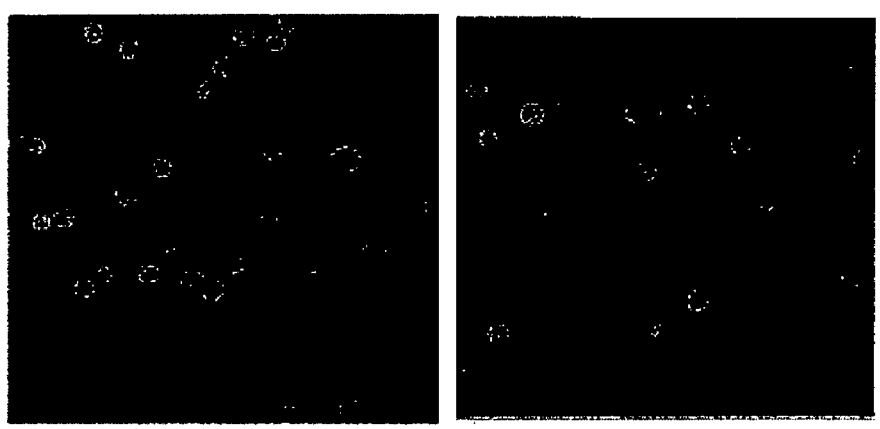

As shown in FIG. 11, the normal cell line NOSE was found to have nuclei stained in green. In contrast, the tumor cell lines NIH:OVCAR-3 and SKOV-3 showed nuclei stained in red at higher frequency than the normal cell line. These results indicate that the anticancer composition of the present invention induces apoptosis in a tumor cell-specific manner.

EXAMPLE 13

Evaluation of Cellular Morphological Change According to Treatment with the Anticancer Composition of the Present Invention Morphological change in cells treated with the anticancer composition of the present invention was observed under a fluorescence microscope after DNA staining.

WI 38, NIH:OVCAR-3 and SKOV-3 cell lines were treated with 100 ml of the anticancer composition prepared in Example 1 (the anticancer composition 4 of Table 1), and incubated for 6 hrs according to the same method as in Example 3. The cells were washed with PBS, and the detached cells were resuspended in PBS. Then, the cellular DNA was stained with 2 μg/ml of Hoechst 33342 (Sigma, U.S.A.) at 37° C. for 30 min in a dark room. After washing with PBS, the cells were observed under a microscope (Olympus Optical Co., Ltd., U.S.A.), the resulting images were captured using the AX70 TRF photoautomated system (Olympus Optical Co., Ltd., U.S.A). In addition, images of nuclear chromatin condensation, morphology of membrane vesicles and apoptotic bodies were obtained using a scanning confocal microscope $\lambda_{exc}$=488 nm, $\lambda_{em}$=522 nm; Bio-Rad, Richmond, Calif., U.S.A.).

Figure 12:
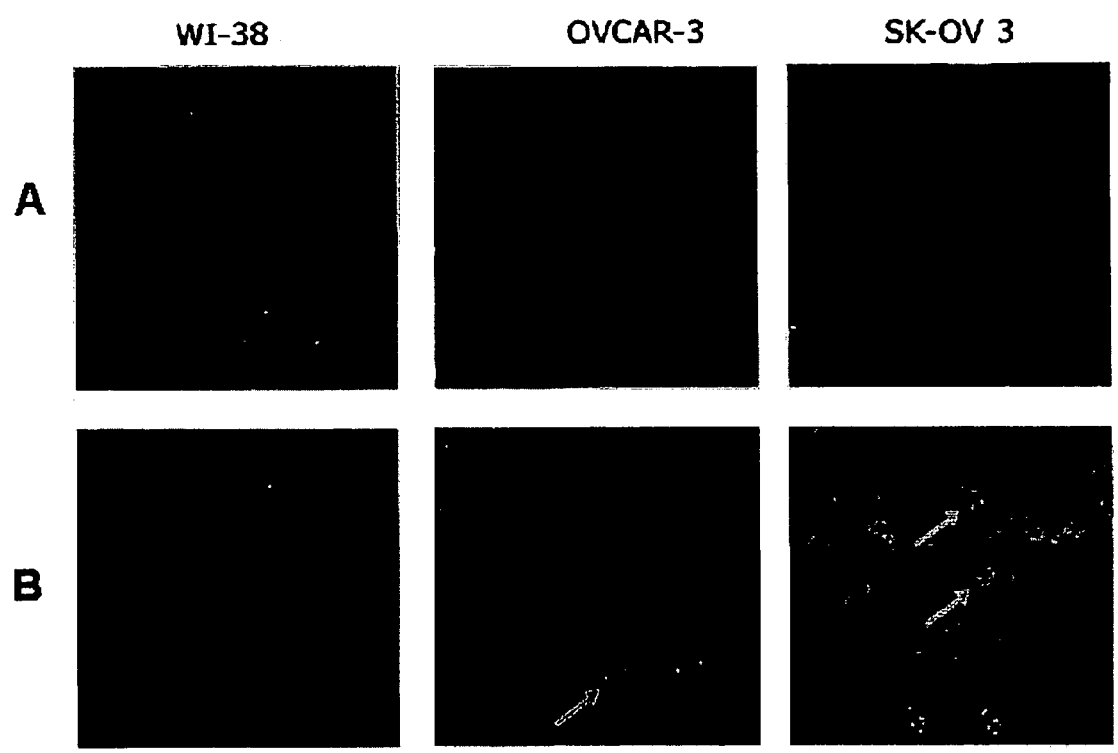
FIG. 12 is a photograph showing a result of fluorescence microscopic analysis of the human ovarian surface normal epithelial cell line NOSE, the human lung fibroblast cell line WI 38 and the human ovarian adenocarcinoma cell line SKOV-3, treated with an anticancer composition comprising citric acid, zinc and albumin as active components according to the present invention, or not (A: not treated with the anticancer composition of the present invention; and B: treated with the anticancer composition of the present invention).

As shown in FIG. 12, in WI 38 cell line treated with the anticancer composition of the present invention, morphological change was not found. In NIH:OVCAR-3 and SKOV-3 cells, when being not treated with the anticancer composition of the present invention, healthy nuclei were observed, while nuclear morphological changes (for example, chromatin condensation, nuclear fragmentation and nuclear compaction) were observed when being treated with the anticancer composition of the present invention. These apoptotic morphological changes of tumor cells were clearly observable using a scanning confocal microscope. As a result, the edge of condensed chromatin lumps was found to be incomplete, and the condensed chromatin was irregularly scattered in the nucleus. On the other hand, the cells maintained their overall morphology despite cytoplasmic modification and destruction of the cytoplasmic membrane.

EXAMPLE 14

In Vivo Assay Determining Effects of the Anticancer Composition of the Present Invention in Tumor-Induced Mouse Model To investigate in vivo effect of the anticancer composition of the present invention, tumor-induced nude mice (BALB-c, Charles River Inc., Japan) was used. Tumors were induced in BALB-c mice by subcutaneous injection of SKOV-3 cells. That is, after being adapted to a new environment under aseptic conditions, five mice (female, 4-week) were injected twice with $3\times10^6$ SKOV-3 cells suspended in 200 μl of PBS through both sides of their back. When tumors had grown to 1 cm in diameter at both injection sites, one tumor was injected with 200 μl of the anticancer composition of the present invention (the anticancer composition 4 of Table 1), and the other was injected with an equal volume of PBS. After 24 hrs, after sacrificing the mice, tumors, lungs, heart, liver and kidney were excised, fixed with 10% formalin, and stained with hematoxylin and eosin (H&E) to perform histological study.

Figure 13:
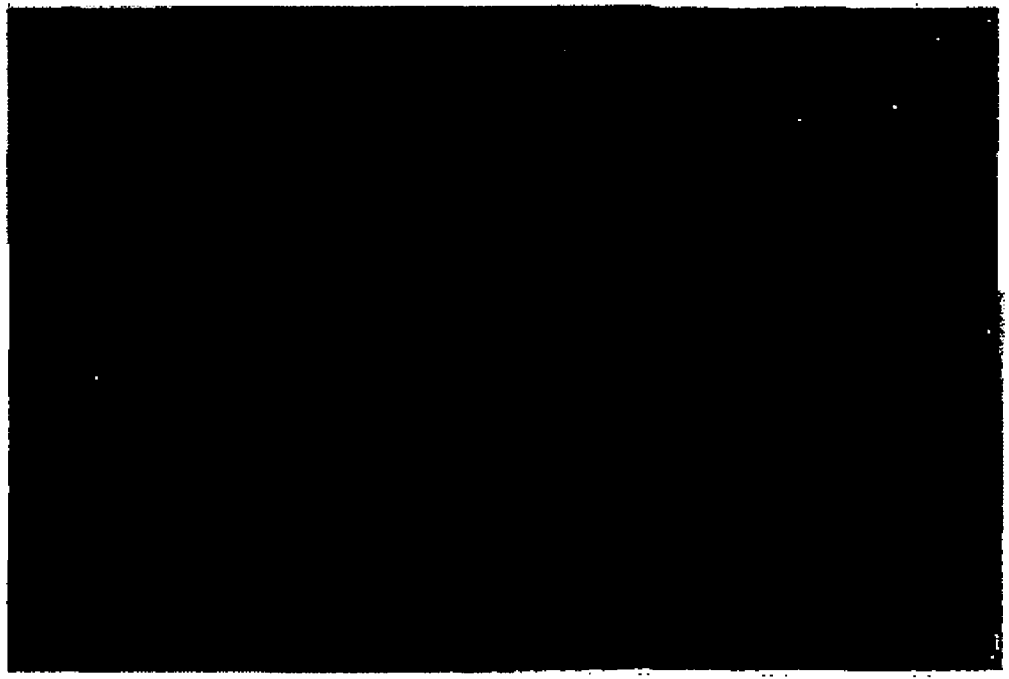
FIG. 13 is a histological photograph showing incidence of subcutaneous tumor or not in mouse, treated with an anticancer composition comprising citric acid, zinc and albumin as active components according to the present invention, or not (A: not treated with the anticancer composition of the present invention; and B: treated with the anticancer composition of the present invention).
Figure 13:
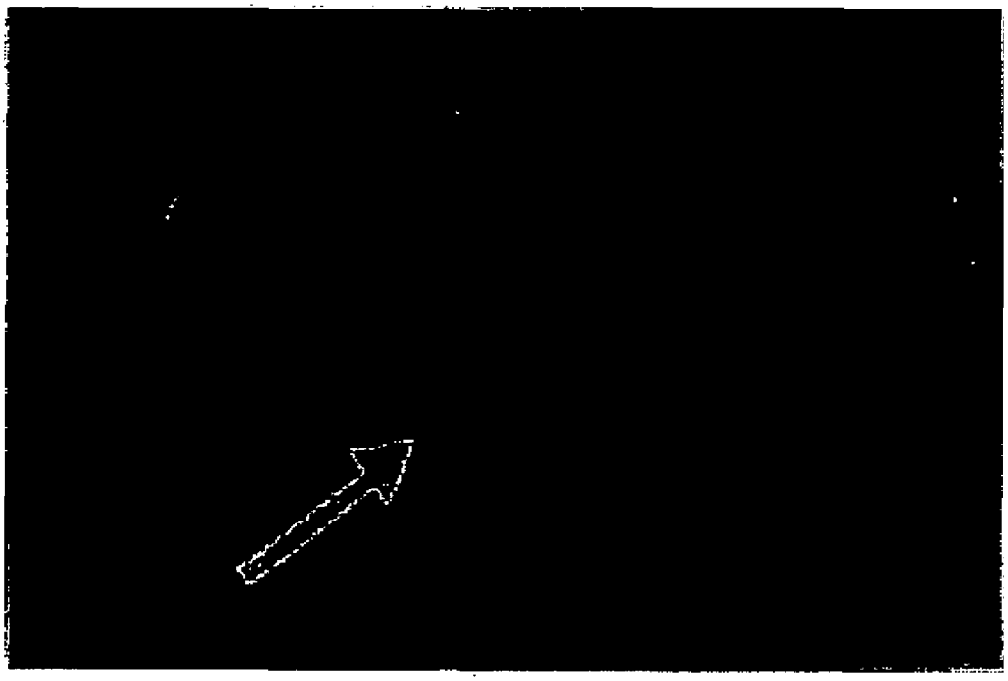

As shown in FIG. 13, when injecting the anticancer composition of the present invention to the tumor-induced mice, tumor cell death was found to occur by apoptosis. In contrast, no damage was found in other tissues except for tumor sites.

What is claimed is:

1. A method of treating cancer, comprising: administering to a patient an anticancer composition comprising:
   (i) a therapeutically effective amount of citric acid in an amount of at least 0.1 weight percent of total weight of said composition;
   (ii) a therapeutically effective amount of zinc in an amount of 0.01 weight percent of total weight of said composition;
   (iii) a therapeutically effective amount of albumin in an amount of at least about 0.01 weight percent of the total weight of said composition; and
   (iv) a pharmaceutically acceptable carrier, wherein said step of administrating is effective to induce apoptosis of tumor cells of said patient, and wherein said step of administrating comprises injecting into the tumor itself of a patient with a daily dose of between 1 and 5 mg of said composition up to 5 times a day.

2. The method of claim 1, wherein said step of administering comprises providing an oral dose to said patient in an amount of between 1 mg and 2,000 mg up to 5 times per day.

* * * * *